US008795657B2

(12) United States Patent
Epshtein (10) Patent No.: US 8,795,657 B2
(45) Date of Patent: Aug. 5, 2014

(54) COMBINATION PHARMACEUTICAL COMPOSITION AND METHODS OF TREATING DISEASES OR CONDITIONS ASSOCIATED WITH RESPIRATORY DISEASE OR CONDITION (75) Inventor: Oleg Iliich Epshtein, Moscow (RU)

(73) Assignee: Oleg I. Epshtein (RU)

( * ) Notice: Subject to any disclaimer, the term of this patent is extended or adjusted under 35 U.S.C. 154(b) by 0 days.

(21) Appl. No.: 13/135,884

(22) Filed: Jul. 15, 2011

(65) Prior Publication Data

US 2012/0225074 A1 Sep. 6, 2012

(30) Foreign Application Priority Data

Jul. 21, 2010 (RU) ................................ 2010130352
Jun. 24, 2011 (RU) ................................ 2011125992

(51) Int. Cl.
*A61K 39/395* (2006.01)
(52) U.S. Cl.
USPC ..................................................... 424/130.1
(58) Field of Classification Search
CPC .................................................. A61K 41/0004
See application file for complete search history.

(56) References Cited

U.S. PATENT DOCUMENTS

| 5,629,286 | A | 5/1997 | Brewitt |
| 5,683,712 | A | 11/1997 | Cavazza |
| 5,741,488 | A | 4/1998 | Feldman et al. |
| 7,229,648 | B2 | 6/2007 | Dreyer |
| 7,572,441 | B2 | 8/2009 | Epshtein et al. |
| 7,582,294 | B2 | 9/2009 | Epshtein et al. |
| 7,700,096 | B2 | 4/2010 | Epshtein et al. |
| 7,815,904 | B2 | 10/2010 | Epshtein et al. |
| 7,923,009 | B2 | 4/2011 | Epshtein et al. |
| 8,066,992 | B2 | 11/2011 | Epshtein |
| 8,168,182 | B2 | 5/2012 | Epshtein |
| 8,178,498 | B1 | 5/2012 | Ephstein |
| 8,241,625 | B2 | 8/2012 | Epshtein et al. |
| 8,524,229 | B2 | 9/2013 | Epshtein et al. |
| 8,535,664 | B2 | 9/2013 | Epshtein et al. |
| 8,617,555 | B2 | 12/2013 | Epshtein |
| 8,637,030 | B2 | 1/2014 | Epshtein |
| 8,637,034 | B2 | 1/2014 | Epshtein |
| 2007/0123518 | A1 | 5/2007 | Epshtein |
| 2007/0224187 | A1 | 9/2007 | Epshtein et al. |
| 2008/0019982 | A1 | 1/2008 | Epshtein et al. |
| 2008/0025985 | A1 | 1/2008 | Epshtein et al. |
| 2008/0050360 | A1 | 2/2008 | Epshtein et al. |
| 2008/0131440 | A1 | 6/2008 | Epshtein et al. |
| 2010/0166762 | A1 | 7/2010 | Epshtein |
| 2010/0203059 | A1 | 8/2010 | Epshtein |
| 2010/0221258 | A1 | 9/2010 | Epshtein |
| 2010/0239569 | A1 | 9/2010 | Epshtein |
| 2010/0260742 | A1 | 10/2010 | Epshtein et al. |
| 2011/0086037 | A1 | 4/2011 | Epshtein |
| 2012/0219556 | A1 | 8/2012 | Epshtein |
| 2012/0282265 | A1 | 11/2012 | Epshtein et al. |
| 2013/0004574 | A1 | 1/2013 | Epshtein |
| 2013/0045237 | A1 | 2/2013 | Epshtein et al. |
| 2013/0058981 | A1 | 3/2013 | Epshtein |
| 2013/0064860 | A1 | 3/2013 | Epshtein |
| 2013/0302312 | A1 | 11/2013 | Epshtein et al. |
| 2013/0303735 | A1 | 11/2013 | Epshtein et al. |
| 2013/0336985 | A1 | 12/2013 | Epshtein et al. |
| 2014/0056923 | A9 | 2/2014 | Epshtein et al. |

FOREIGN PATENT DOCUMENTS

| EP | 0687466 A1 | 12/1995 |
| RU | 2191602 C1 | 10/2002 |
| RU | 2197266 C1 | 1/2003 |
| RU | 2199344 C1 | 2/2003 |
| RU | 2199345 C1 | 2/2003 |
| RU | 2206338 C1 | 6/2003 |
| RU | 2209083 C1 | 7/2003 |
| WO | 9814161 A1 | 4/1998 |
| WO | 9833493 A1 | 8/1998 |

OTHER PUBLICATIONS

English translation of Abstract of Foreign Patent Document RU2206338, (2003).
English translation of Abstract of Foreign Patent Document RU2209083, (2003).
English translation of Abstract of Foreign Patent Document RU2199344, (2003).
English translation of Abstract of Foreign Patent Document RU2191602, (2002).
English translation of Abstract of Foreign Patent Document RU2199345, (2003).
Super Low Doses of Antibodies to Inflammation Mediators: Antitussive Properties of Antibodies to Bradykinin, Histamine and Serotonin, O. I. Epshtein, V. L. Kovaleva, M. S. Zak, Yu. L. Dugina, Byulleten' eksperimental'noi biologii i meditsiny, 2003, appendix No. 1.
English translation of Abstract of Super Low Doses of Antibodies to Inflammation Mediators: Antitussive Properties of Antibodies to Bradykinin, Histamine and Serotonin, O. I. Epshtein, V. L. Kovaleva, M. S. Zak, Yu. L. Dugina, Byulleten' eksperimental'noi biologii i meditsiny, 2003, appendix No. 1.
Antitussive Activity of the Preparations Anar and Prohistam During Separate and Combined Use on a Cough Model Caused by Capsaicin, V. L. Kovaleva, I. A. Kheifets, Yu. L. Dugina, S. A. Sergeeva, O. I. Epshtein, 15th Russian National Congress on Man and Medicine Collection of papers from a congress. Abstracts of reports. Moscow, Apr. 14-18, 2008.
English translation of Abstract of Antitussive Activity of the Preparations Anar and Prohistam During Separate and Combined Use on a Cough Model Caused by Capsaicin, V. L. Kovaleva, I. A. Kheifets, Yu. L. Dugina, S. A. Sergeeva, O. I. Epshtein, 15th Russian National Congress on Man and Medicine Collection of papers from a congress. Abstracts of reports. Moscow, Apr. 14-18, 2008.

(Continued)

Primary Examiner — Ilia Ouspenski
(74) Attorney, Agent, or Firm — Pergament Gilman & Cepeda LLP (57) ABSTRACT The present invention is concerned with a combination pharmaceutical composition comprising a) an activated-potentiated form of an antibody to bradykinin, b) an activated-potentiated form of an antibody to histamine and c) an activated-potentiated form of an antibody to morphine and method for treating and preventing upper respiratory tract conditions or disorders and the symptoms associated therewith by administration of the combination composition.

11 Claims, 2 Drawing Sheets (56) References Cited

OTHER PUBLICATIONS

Antitussive Activity of the Preparations Anar and Prohistam During Separate and Combined Use, V. L. Kovaleva, I. A. Kheifets, Yu. L. Dugina, S. A. Sergeeva, O. I. Epshtein, 14th Russian National Congress Man and Medicine Collection of papers from a congress. Abstracts of reports. Apr. 16-20, 2007, Moscow.

English translation of Abstract of Antitussive Activity of the Preparations Anar and Prohistam During Separate and Combined Use, V. L. Kovaleva, I. A. Kheifets, Yu. L. Dugina, S. A. Sergeeva, O. I. Epshtein,14th Russian National Congress Man and Medicine Collection of papers from a congress. Abstracts of reports. Apr. 16-20, 2007, Moscow.

Antitussive Activity of the Preparations Anar and Prohistam During Separate and Combined Use on a Cough Model Caused by Capsaicin, V. L. Kovaleva, I. A. Kheifets, Yu. L. Dugina, S. A. Sergeeva, O. I. Epshtein, Second National Congress of Therapists New course: Consolidation of Efforts for National Health Protection Collection of papers, Moscow, Nov. 7-9, 2008.

English translation of Abstract of Antitussive Activity of the Preparations Anar and Prohistam During Separate and Combined Use on a Cough Model Caused by Capsaicin, V. L. Kovaleva, I. A. Kheifets, Yu. L. Dugina, S. A.Sergeeva, O. I. Epshtein, Second National Congress of Therapists New course: Consolidation of Efforts for National Health Protection Collection of papers, Moscow, Nov. 7-9, 2008.

Anti-Inflammatory Effect of the Preparations Anar and Prohistam During Separate and Combined Use Under Conditions of Inflammation Caused by Bradykinin, V. L. Kovaleva, I. A. Kheifets, Yu. L. Dugina, S. A. Sergeeva, O. I. Epshtein 14th Russian National Congress Man and Medicine Collection of papers from a congress, abstracts of reports, Moscow, Apr. 16-20, 2007.

English translation of Abstract of Anti-Inflammatory Effect of the Preparations Anar and Prohistam During Separate and Combined Use Under Conditions of Inflammation Caused by Bradykinin, V. L. Kovaleva, I. A. Kheifets, Yu. L. Dugina, S. A. Sergeeva, O. I. Epshtein, 14th Russian National Congress Man and Medicine Collection of papers from a congress, abstracts of reports, Moscow, Apr. 16-20, 2007.

Kovaleva et al., Antitussive Activity of the Preparations Anar and Prohistam During Separate and Combined Use on a Cough Model Caused by Capsaicin, 15th Russian National Congress on Man and Medicin, Abstracts (Apr. 14-18, 2008)(English translation of previously disclosed NPL).

Notification of Transmittal of International Search Report and Written Opinion dated Feb. 27, 2012, for corresponding International Patent Application No. PCT/IB2011/002346.

International Search Report dated Feb. 27, 2012, for corresponding International Patent Application No. PCT/IB20111002346.

Written Opinion of the International Searching Authority dated Feb. 27, 2012, for corresponding International Patent Application No: PCT/IB2011/002346.

Written Opinion of the International Preliminary Examining Authority dated Jul. 17, 2012, for corresponding International Patent Application No: PCT/IB2011/002346.

Notification of Transmittal of the International Preliminary Report on Patentability dated Oct. 15, 2012, for corresponding International Patent Application No: PCT/IB2011/002346.

International Preliminary Report on Patentability dated Oct. 15, 2012, for corresponding International Patent Application No. PCT/IB2011/002346.

Linde, et al., "Are the Clinical Effects of Homoeopathy Placebo Effects? A Meta-Analysis of Placebo-Controlled Trials", The Lancet, Sep. 20, 1997, p. 834-843, vol. 350, No. 9081.

Enserink, M, "French Nobelist Escapes "Intellectual Terror" to Pursue Radical Ideas in China", Science, Dec. 24, 2010, p. 1732-1732, vol. 330, No. 6012.

Declaration of Dr. Oleg I. Epshtein under 37 CFR 1.132 dated Dec. 10, 2008, for U.S. Appl. No. 10/522,652.

Klein-Seetharaman, "Interim Report #1: Mechanism Action of Anaferon for Children: Allosteric Modulation of Interferon Gamma", Jun. 20, 2011, p. 1-11.

Epstein, et al., "Antitussive Activity of Anar.", Bulletin of Experimental Biology and Medicine, Jan. 2003, p. 96-98, vol. 135, Suppl. 7, LNKD- PUBMED:12949665.

Jonas, et al., "A Critical Overview of Homeopathy", Annals of Internal Medicine, Mar. 4, 2003, p. 393-399, vol. 138, No. 5, New York, NY.

Vickers, "Clinical Trials of Homeopathy and Placebo: Analysis of a Scientific Debate", The Journal of Alternative and Complementary Medicine, Feb. 1, 2000 (Feb. 1, 2000), p. 49-56, vol. 6, No. 1, Mary Ann Lieber, Inc., New York, NY.

Guggisberg, et al., "Replication Study Concerning the Effects of Homeopathic Dilutions of Histamine on Human Basophil Degranulation in Vitro", Complementary Therapies in Medicine, Jun. 1, 2005 (Jun. 1, 2005), p. 91-100, vol. 13, No. 2, Churchill Livingstone, Edinburgh, GB.

McMillan, F.D., "The Placebo Effect in Animals", Journal of the American Veterinary Medical Association, Oct. 1, 1999, p. 992-999, vol. 215, No. 7.

Davenas, et al., "Human Basophil Degranulation Triggered by Very Dilute Antiserum Against IgE", Nature, Jun. 1988, vol. 333, p. 816-818.

Shang, et al., "Are the Clinical Effects of Homoeopathy Placebo Effects? Comparative Study of Placebo-Controlled Trials of Homoeopathy and Allopathy", The Lancet, Aug. 27, 2005 (Aug. 27, 2005), pp. 726-732, vol. 366, No. 9487, Lancet Limited, London, GB.

Epshtein, et al., "Effect of Potentiated Antibodies to Brain-Specific Protein S100 on the Integrative Activity of the Brain", Bulletin of Experimental Biology and Medicine, May 1999, No. 5, p. 493-495.

Epstein, et al., "Psychotropic Drug Tenoten Activates Mitogen-Activated MAP/ERK Kinase Regulatory Cascade Controlling the Neuroprotective Effects", Bulletin of Experimental Biology and Medicine, 2007, vol. 144, No. 3, p. 319-321.

Beregovoy, et al., "On Influence of Various Dilutions of Monoclonal Antibodies 5F5-B6 on the Formation of Long-Term Post — Tetanic Potentiation in Survived Hippocampal Slices", Bulletin of Siberian Branch of RAMS, 1999, No. 1, p. 91-96.

Epshtein, et. al., "Effects of Potentiated Antibodies to Brain Specific Protein S100 on the Dynamics of Long-Term Potentiation in Hippocampal Slices", Bulletin of Experimental Biology and Medicine, 1999, No. 3, p. 286-289.

Thorsell, Annika, "Brain Neuropeptide Y and Corticotropin-Releasing Hormone in Mediating Stress and Anxiety", Experimental Biology and Medicine, 2010, p. 1163-1167.

Zapara, et al., "Potentiated Morphine Effect on the Electric Properties of Isolated Neurons", Bulletin of Siberian Branch of RAMS, 1999, No. 1, p. 1-3.

Guha, et al., "Bradycardia, Reversible Panconduction Defect and Syncope following Self-Medication with a Homeopathic Medicine", Cardiology, 1999, p. 268-271.

COMBINATION PHARMACEUTICAL COMPOSITION AND METHODS OF TREATING DISEASES OR CONDITIONS ASSOCIATED WITH RESPIRATORY DISEASE OR CONDITION

FIELD

A combination pharmaceutical composition comprising (a) an activated-potentiated form of an antibody to bradykinin, (b) an activated-potentiated form of an antibody to histamine and (c) an activated-potentiated form of an antibody to morphine and methods of treating acute and chronic respiratory tract disorders or conditions and symptoms of cough.

BACKGROUND

Human respiratory tract infections and cough have caused widespread suffering for centuries. These infections are generally believed to be caused by microorganisms such as a bacteria and viruses which can be either airborne or transmitted via direct contact. The early stages of infection are usually characterized by congestion of the sinuses, often accompanied by profuse mucous production. Subsequently, the infection can spread downward to the throat, bronchi and lungs. The common cold, one of mankind's most frequent disease afflictions (also called non-allergic rhinitis, viral upper respiratory tract infection, viral URI) is a contagious infectious disease that has long been a source of suffering with expenditures of time and money, as well as a leading cause of doctor visits.

While many treatments have been proposed and utilized for treating and/or preventing upper respiratory tract infections and their symptoms, their efficacy and side effects have left much to be desired. Antibiotics, which are prescribed with disturbing frequency by practitioners are ineffective both theoretically and in practice since the common cold is caused by a virus, not a bacteria (Gonzales R, et al "*Antibiotic prescribing for adults with colds, upper respiratory tract infections, and bronchitis by ambulatory care physicians*", JAMA Sep. 17, 1997; 278(11) 901-4; Mainous A. G., et al, "*Antibiotics and upper respiratory infection: do some folks think there is a cure for the common cold?*" J Fam Pract 1996 April; 42 (4); 357-61). Over-the-counter cold prescriptions invariably act to suppress symptoms locally through actions against such agents as histamine (the antihistamine group of drugs, for example, Benadryl) or through various actions on the autonomic nervous system (such as ephedrine).

The act of coughing is a protective reflex. However, persistent cough is abnormal and it often due to URTI. Coughing may dramatically affect one's quality of life when it becomes excessive and/or profound. It has been demonstrated that over the counter cough suppressants and expectorants have proven to be ineffective. Furthermore, many of these medications have been demonstrated to cause adverse side effects, especially in children. The only prescription cough medicine proven to be beneficial, according to The American College of Chest Physicians, is codeine. However, it has been documented that prescribed codeine derivative products suppress cough only at doses that cause side effects, such as gastrointestinal constipation, sedation, and respiratory depression. There exist few, if any, pharmaceutical products that have been found to address cough.

Thus, there is a need for an agent effective in preventing and/or treating upper respiratory infections, including the common cold and symptoms thereof. The present invention concerns such an agent and a method of preventing and/or treating upper respiratory diseases or conditions and symptoms thereof.

The therapeutic effect of an extremely diluted form (or ultra-low form) of antibodies potentized by homeopathic technology (activated-potentiated form) has been discovered by the inventor of the present patent application, Dr. Oleg I. Epshtein. U.S. Pat. No. 7,582,294 discloses a medicament for treating Benign Prostatic Hyperplasia or prostatitis by administration of a homeopathically activated form of antibodies to prostate specific antigen (PSA).

Kinins are low-molecular-weight peptides that participate in inflammatory processes by virtue of their ability to activate endothelial cells and, as a consequence, lead to vasodilatation, increased vascular permeability, production of nitric oxide, and mobilization of arachidonic acid. Bradykinin is the best characterized of this group of vasoactive substances. Kaplan A P, Joseph K, Silverberg M. *Pathways for bradykinin formation and inflammatory disease*. J Allergy Clin Immunol. 2002 February 109(2):195-209.

Bradykinin is released when inflammation, trauma, burn injury, shock, allergy, and specific cardiovascular disease occur. Once released, bradykinin initiates or increases the secretion of a mediator, which stimulates sensory afferent nerve endings, from leukocyte.

Receptors for bradykinin play an important role in the induction of cough. Bradykinin possesses vasoactive properties and induces cough by affecting the mucosal layer of the upper respiratory tract. Epstein et al., *Ultralow doses of antibodies to inflammatory mediators: Antitussive properties of antibodies to bradykinin, histamine and serotonin*, Bulletin of Experimental Biology and Medicine, Supplement 1, 2003, pgs 146-149. Ultralow doses of antibodies to bradykinin are known. Epstein et al., 2003.

Histamines are implicated in a number of medical conditions, including inflammation, asthma, allergy, atopic dermatitis and chronic obstructive pulmonary disease (COPD). Histamine produces its actions by an effect on specific histamine receptors which are of four main types, H1, H2, H3 and H4. Specific histamine receptor subtypes are involved in specific medical conditions. H1 receptor antagonists (antihistamines) are widely used for treating allergic reactions including allergic rhinitis (hay fever), urticaria, insect bites and drug hypersensitivities. H2 receptor antagonists are frequently used as inhibitors of gastric acid secretion. They are used as the drugs of choice in the treatment of peptic ulcer, as second line drugs in the treatment of Zollinger-Ellison syndrome and for treating reflux oesophagitis. H3 appeared to regulate the vestibular inputs (Chavez 2005). H4 receptor appears to be involved in inflammatory actions.

Ultra low doses of antibodies to histamine have been shown to have Antiulcer activity, Krylova et al., *Antiulcer activity of ultralow doses of antibodies to histamine under experimental conditions*, Bull Exp Biol Med 2003 January; 135 Suppl 7:80-2.

Morphine is a potent narcotic analgesic which is principally used to relieve pain. Morphine is used also in the management of dyspnea of heart failure, in pulmonary edema and cough, as a sedative, and in the control of diarrhea. Morphine most significant actions are analgesic, hypnosis, respiratory depression, central nervous system depressant effects, and as a local anesthetic. Morphine is administered effectively by injection, but a pharmaceutically acceptable material means for administering morphine orally as an analgesic, as an adjunct to anesthesia, as an antitussive, and a nonspecific antidiarrheal therapy appears to be lacking in the pharmaceutical and medical arts.

Ultra low doses of antibodies to morphine are known. Beregovoi, et al., *Effect of antibodies to morphine in ultralow doses on induction of long-term potentiation in hippocampal slices from rats with chronic morphine dependence*, Bull Exp Biol Med. 2003 January; 135 Suppl 7:26-8.

There is a continuous need for new treatment for respiratory disorders and cough.

SUMMARY

The present invention is concerned with a composition and method for treating and preventing upper respiratory tract conditions or disorders and the symptoms associated therewith.

In one aspect, the invention provides a combination pharmaceutical composition comprising a) an activated-potentiated form of an antibody to bradykinin, b) an activated-potentiated form of an antibody to histamine and c) an activated-potentiated form of an antibody to morphine.

In one variant, the present invention provides a combination pharmaceutical composition comprising a) an activated-potentiated form of an antibody to bradykinin, b) an activated-potentiated form of an antibody to histamine and c) an activated-potentiated form of an antibody to morphine, wherein the antibody is to the entire bradykinin or fragments thereof.

In one variant, the present invention provides a combination pharmaceutical composition comprising a) an activated-potentiated form of an antibody to bradykinin, b) an activated-potentiated form of an antibody to histamine and c) an activated-potentiated form of an antibody to morphine, wherein the antibody is to the entire histamine or fragments thereof.

In one variant, the combination pharmaceutical composition of this aspect of the invention includes activated-potentiated form of an antibody to bradykinin is in the form of a mixture of (C12, C30, and C50) or (C12, C30 and C200) homeopathic dilutions impregnated onto a solid carrier. The activated-potentiated form of an antibody to histamine is in the form of mixture of (C12, C30, and C50) or (C12, C30 and C200) homeopathic dilutions may be subsequently impregnated onto the solid carrier. The activated-potentiated form of an antibody to morphine is in the form of mixture of (C12, C30, and C50) or (C12, C30 and C200) homeopathic dilutions may be subsequently impregnated onto the solid carrier.

In one variant, the combination pharmaceutical composition of this aspect of the invention includes activated-potentiated form of an antibody to histamine is in the form of a mixture of (C12, C30, and C50) or (C12, C30 and C200) homeopathic dilutions impregnated onto a solid carrier. The activated-potentiated form of an antibody to bradykinin is in the form of mixture of (C12, C30, and C50) or (C12, C30 and C200) homeopathic dilutions may be subsequently impregnated onto the solid carrier. The activated-potentiated form of an antibody to morphine is in the form of mixture of (C12, C30, and C50) or (C12, C30 and C200) homeopathic dilutions may be subsequently impregnated onto the solid carrier.

In one variant, the combination pharmaceutical composition of this aspect of the invention includes activated-potentiated form of an antibody to morphine is in the form of a mixture of (C12, C30, and C50) or (C12, C30 and C200) homeopathic dilutions impregnated onto a solid carrier. The activated-potentiated form of an antibody to bradykinin is in the form of mixture of (C12, C30, and C50) or (C12, C30 and C200) homeopathic dilutions may be subsequently impregnated onto the solid carrier. The activated-potentiated form of an antibody to histamine is in the form of mixture of (C12, C30, and C50) or (C12, C30 and C200) homeopathic dilutions may be subsequently impregnated onto the solid carrier.

Preferably, the activated-potentiated form of an antibody to bradykinin is a monoclonal, polyclonal or natural antibody, more preferably, a polyclonal antibody. In one variant of this aspect of the invention, the activated-potentiated form of an antibody to bradykinin is prepared by successive centesimal dilutions coupled with shaking of every dilution.

Preferably, the activated-potentiated form of an antibody to histamine is a monoclonal, polyclonal or natural antibody, more preferably, a polyclonal antibody. In one variant of this aspect of the invention, the activated-potentiated form of an antibody to histamine is prepared by successive centesimal dilutions coupled with shaking of every dilution.

Preferably, the activated-potentiated form of an antibody to morphine is a monoclonal, polyclonal or natural antibody, more preferably, a polyclonal antibody. In one variant of this aspect of the invention, the activated-potentiated form of an antibody to morphine is prepared by successive centesimal dilutions coupled with shaking of every dilution.

In another aspect, the invention provides a method of treating a respiratory disease or condition, said method comprising administering to a patient in need thereof a) an activated-potentiated form of an antibody to bradykinin, b) an activated-potentiated form of an antibody to histamine and c) an activated-potentiated form of an antibody to morphine. Preferably, the activated-potentiated form of an antibody to bradykinin, the activated-potentiated form of an antibody to histamine and the activated-potentiated form of an antibody to morphine are administered in the form of combined pharmaceutical composition.

In another aspect, the invention provides a method of treating a patient suffering from respiratory tract disorders or conditions, by administration of a combination pharmaceutical composition wherein the composition comprises a) an activated-potentiated form of an antibody to bradykinin, b) an activated-potentiated form of an antibody to histamine and c) an activated-potentiated form of an antibody to morphine.

In one variant the respiratory tract disorder or condition is viral respiratory tract infection.

In another variant the respiratory tract disorder or condition is acute upper respiratory tract disorder.

In another variant the respiratory tract disorder or condition is chronic upper respiratory tract disorder.

In another aspect, the invention provides a method of treating a patient suffering from symptoms of upper respiratory tract disorder or condition, by administration of a combination pharmaceutical composition wherein the composition comprises a) an activated-potentiated form of an antibody to bradykinin, b) an activated-potentiated form of an antibody to histamine and c) an activated-potentiated form of an antibody to morphine.

In one variant the symptom of respiratory tract disorder or condition is cough.

In one variant of the invention, there is provided administration of from one to two unit dosage forms of the activated-potentiated form of an antibody to bradykinin, one to two unit dosage forms of the activated-potentiated form of an antibody to histamine and from one to two unit dosage forms of the activated-potentiated form of an antibody to morphine, each of the dosage form being administered from once daily to four times daily. Preferably, the one to two unit dosage forms of each of the activated-potentiated forms of antibodies is administered twice daily.

In a preferred variant of this aspect of the invention, there is provided administration of from one to two unit dosage forms, of the combination composition comprising a) an activated-potentiated form of an antibody to bradykinin, b) an activated-potentiated form of an antibody to histamine and c) an activated-potentiated form of an antibody to morphine, each of the dosage form being administered from once daily to four times daily. Preferably, one to two unit dosage forms are administered twice daily.

In another variant of this aspect of the invention, which is preferred, the combination is administered in the form of one unit dosage form comprising a) an activated-potentiated form of an antibody to bradykinin, b) an activated-potentiated form of an antibody to histamine and c) an activated-potentiated form of an antibody to morphine, preferably twice daily.

DETAILED DESCRIPTION

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and $F(ab')_2$, Fab', and the like. The singular "antibody" includes plural "antibodies."

The term "activated-potentiated form" or "potentiated form" respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, 'homeopathic potentization" may involve, for example, repeated consecutive dilutions combined with external treatment, particularly (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions (C12, C30, and C200) or the use of the mixture of three aqueous or aqueous-alcohol dilutions of the primary matrix solution of antibodies diluted $100^{12}$, $100^{30}$ and $100^{50}$ times, respectively, which is equivalent to centesimal homeopathic dilutions (C12, C30 and C50). Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term 'activated-potentiated" form used in the claims.

In other words, an antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 and 4,311,897, which are incorporated by reference in their entirety and for the purpose stated, describe such processes that are well accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model. Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200 or the mixture of three aqueous or aqueous-alcohol dilutions of the primary matrix solution (mother tincture) of antibodies diluted $100^{12}$, $100^{30}$ and $100^{50}$ times, respectively, which is equivalent to centesimal homeopathic dilutions C12, C30 and C50. Examples of how to obtain the desired potency are also provided, for example, in U.S. Pat. Nos. 7,229,648 and 4,311,897, which are incorporated by reference for the purpose stated. The procedure applicable to the "activated potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein are tested for biological activity in well accepted pharmacological models of activity, either in appropriate in vitro experiments, or in vivo in suitable animal models. The experiments provided further below provide evidence of biological activity in such models. Human clinical studies also provide evidence that the activity observed in the animal model is well translated to human therapy. Human studies have also provided evidence of availability of the "activated potentiated" forms described herein to treat specified human diseases or disorders well accepted as pathological conditions in the medical science.

Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of s the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid form in which the concentration of the initial molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the initial molecular form of the antibody is below the Avogadro number. In the pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model.

The term "cough intensity scale" denotes the questionnaire for subjective assessment of cough severity during daytime and nighttime by patients and consisting of the following questions rated from 0 to 5 points:

Daytime
0 points—No cough
1 point—Cough for one short period
2 points—Cough for more than two short periods
3 points—Frequent cough not interfering with usual activities
4 points—Frequent cough interfering with usual activities
5 points—Distressing cough most of the day Night-Time
0 points—No cough
1 point—Cough on waking only/cough on going to sleep only
2 points—Awoken once or woken early due to coughing
3 points—Frequent waking due to coughing
4 points—Frequent coughs most of the night
5 points—Distressing cough.

The present invention provides a combination pharmaceutical composition comprising a) an activated-potentiated form of an antibody to bradykinin, b) an activated-potentiated form of an antibody to histamine and c) an activated-potentiated form of an antibody to morphine. As set forth herein above, each of the individual components of the combination is generally known for its own individual medical uses. However, the inventors of the present patent application surprisingly discovered that administration of the combination remarkably reduces the symptoms of cough and aids in the treatment of upper respiratory tract disorders or conditions.

The combination pharmaceutical composition in accordance with this aspect of the invention may be in the liquid form or in solid form. Each of the activated potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in Immunotechniques, G. Frimel, M., "Meditsyna", 1987, p. 9-33; and "*Hum. Antibodies. Monoclonal and recombinant antibodies, 30 years after*" by Laffly E., Sodoyer R.—2005—Vol. 14.—N 1-2. P.33-55, both incorporated herein by reference.

Monoclonal antibodies may be obtained, e.g., by means of hybridoma technology. The initial stage of the process includes immunization based on the principles already developed in the course of polyclonal antisera preparation. Further stages of work involve the production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen, either bradykinin, histamine or morphine. The animals' immune system generates corresponding antibodies, which are collected from the animals in a known manner. This procedure enables preparation of a monospecific antibody-rich serum.

If desired, the serum containing antibodies may be purified, for example by using affine chromatography, fractionation by salt precipitation, or ion-exchange chromatography. The resulting purified, antibody-enriched serum may be used as a starting material for the preparation of the activated-potentiated form of the antibodies. The preferred concentration of the resulting initial solution of antibody in the solvent, preferably water or a water-ethyl alcohol mixture, ranges from about 0.5 to about 5.0 mg/ml.

The preferred procedure for preparing each component of the combination drug according to the present invention is the use of the mixture of three aqueous-alcohol dilutions of the primary matrix solution of antibodies diluted $100^{12}$, $100^{30}$ and $100^{50}$ times, respectively, which is equivalent to centesimal homeopathic dilutions C12, C30, and C50 or diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In a preferred embodiment, the starting material for the preparation of the activated potentiated form that comprise the combination of the invention is polyclonal, animal-raised antibody to the corresponding antigen, namely, bradykinin, histamine or morphine. To obtain the activated-potentiated form of polyclonal antibodies to bradykinin, the desired antigen may be injected as immunogen into a laboratory animal, preferably, rabbits. The following sequence of bradykinin is specifically contemplated as suitable antigen:

```
                                        SEQ. ID. NO. 1
    Arg Pro Pro Gly Phe Ser Pro Phe Arg
    1               5               9
```

The exemplary procedure for preparation of the starting polyclonal antibodies to bradykinin may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rotations per minute. Supernatant fluid is the target antiserum. The obtained antiserum is typically yellow. 20% of $NaN_3$ (weight concentration) is added in the antiserum to a final concentration of 0.02% and stored before use in frozen state at the temperature of −20° C. or or without $NaN_3$ at the temperature of −70° C. To separate the target antibodies to bradykinin from the antiserum, the following solid phase absorption sequence is suitable:

10 ml of the antiserum of rabbits is diluted twofold with 0.15 M NaCl, after which 6.26 g $Na_2SO_4$ is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to a DEAE-cellulose column balanced by phosphate buffer. The antibody fraction is determined by measuring the optical density of the eluate at 280 nm.

The isolated crude antibodies are purified using affine chromatography method by attaching the obtained antibodies to bradykinin located on the insoluble matrix of the chromatography media, with subsequent elution by concentrated aqueous salt solutions.

The resulting buffer solution is used as the initial solution for the homeopathic dilution process used to prepare the activated potentiated form of the antibodies. The preferred concentration of the initial matrix solution of the antigen-purified polyclonal rabbit antibodies to bradykinin is 0.5 to 5.0 mg/ml, preferably, 2.0 to 3.0 mg/ml.

Polyclonal antibodies to morphine may be obtained using the above-described methodology similar to methodology used for bradykinin using morphine hemisuccinate conjugated with KLH as the immunogen.

Polyclonal antibodies to histamine, which is a biogenic amine (4-(2-aminoethyl)-imidazole or beta-imidazolyl ethylamine of chemical formula C5H9N3) may be obtained using the above-described methodology using adjuvant and commercially manufactured histamine dihydrochloride.

The activated-potentiated form of each component of the combination may be prepared from an initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution) of a neutral solvent, starting with a concentration of the initial solution of antibody in the solvent, preferably, water or a water-ethyl alcohol mixture, in the range from about 0.5 to about 5.0 mg/ml, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "*Homeopathic medicines*", M., 1967, p. 14-29, incorporated herein by reference for the purpose stated.

For example, to prepare a 12-centesimal dilution (denoted C12), one part of the initial matrix solution of antibodies to bradykinin with the concentration of 3.0 mg/ml is diluted in 99 parts of neutral aqueous or aqueous-alcohol solvent (preferably, 15%-ethyl alcohol) and then vertically shaked many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies to bradykinin with the concentration of 3.0 mg/ml in 99 parts of a neutral solvent in different containers, which is equivalent to the centesimal homeopathic dilution C12. Similar procedures with the relevant dilution factor are performed to obtain dilutions C30, C50 and C200. The intermediate dilutions may be tested in a desired biological model to check activity. The preferred activated potentiated forms for both antibodies comprising the combination of the invention are a mixture of C12, C30, and C50 dilutions or C12, C30 and C200 dilutions. When using the mixture of various homeopathic dilutions (primarily centesimal) of the active substance as biologically active liquid component, each component of the composition (e.g., C12, C30, C50, C200) is prepared separately according to the above-described procedure until the next-to-last dilution is obtained (e.g., until C11, C29, and C199 respectively), and then one part of each component is added in one container according to the mixture composition and mixed with the required quantity of the solvent (e.g. with 97 parts for centesimal dilution).

It is possible to use the active substance as mixture of various homeopathic dilutions, e.g. decimal and/or centesimal (D20, C30, C100 or C12, C30, C50 or C12, C30, C200, etc.), the efficiency of which is determined experimentally by testing the dilution in a suitable biological model, for example, in models described in the examples herein.

In the course of potentiation and concentration decrease, the vertical shaking may be substituted for external exposure to ultrasound, electromagnetic field or any similar external impact procedure accepted in the homeopathic art.

Preferably, the pharmaceutical composition of the invention may be in the form of a liquid or in the solid unit dosage form. The preferred liquid form of the pharmaceutical composition is a mixture, preferably, at a 1:1 ratio of the activated potentiated form of antibodies to bradykinin, the activated potentiated form of antibodies to histamine and the activated potentiated form of antibodies to morphine. The preferred liquid carrier is water or water-ethyl alcohol mixture.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono- oligo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose, magnesium stearate, and citric acid.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies to bradykinin, the activated potentiated form of antibodies to histamine and the activated potentiated form of antibodies to morphine. The preferred carrier is isomalt. The pharmaceutical dosage form may further include standard pharmaceutical excipients, for example, microcrystalline cellulose, magnesium stearate and crospovidone.

The example of preparation of the solid unit dosage form is set forth below.

To prepare the solid oral form, granules of isomalt are impregnated with aqueous or aqueous-alcoholic solutions of the activated potentiated form of antibodies to bradykinin, the activated potentiated form of antibodies to histamine and the activated potentiated form of antibodies to morphine in the ratio of 1 kg of antibody solution to 5 or 10 kg of carrier (1:5 to 1:10). To effect impregnation, the isomalt granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (9.5 to 98 weight parts) saturated with the activated potentiated form of antibodies is placed in the mixer, and is mixed with 2 to 88 weight parts of "non-saturated" pure isomalt (used for the purposes of cost reduction and simplification and acceleration of the technological process without decreasing the treatment efficiency), 0.5 to 0.7 weight parts of sodium cyclamate, 0.1 to 1.5 weight parts of magnesium stearate, 0.05 to 0.07 weight parts of sodicum saccharine and 1 to 1.5 weight parts of citric acid. The obtained tablet mass is uniformly mixed, and tableted by direct dry pressing (e.g., in a Korsch—XL 400 tablet press) to form 150 to 500 mg round pills, preferably 250 mg. After tableting, 250 mg pills are obtained that are saturated with aqueous-alcohol solution (3.0-6.0 mg/pill) of the combination of the activated potentiated form of antibodies to bradykinin, the activated potentiated form of antibodies to histamine and the activated potentiated form of antibodies to morphine. Each component of the combination used to impregnate the carrier is in the form of a mixture of centesimal homeopathic dilutions C12, C30, and C50 or a mixture of centesimal homeopathic dilutions C12, C30 and C200.

In another variant, to prepare the solid oral form, 100-300 μm granules of lactose are impregnated with aqueous or aqueous-alcoholic solutions of the activated potentiated form of antibodies to bradykinin, the activated potentiated form of antibodies to histamine and the activated potentiated form of antibodies to morphine in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch—XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated-potentiated form of antibodies to bradykinin, the activated potentiated form of antibodies to histamine and the activated potentiated form of antibodies to morphine. Each component of the combination used to impregnate the carrier is in the form of a mixture of centesimal homeopathic dilutions C12, C30, and C50 or a mixture of centesimal homeopathic dilutions C12, C30 and C200.

While the invention is not limited to any specific theory, it is believed that the activated potentiated form of the antibodies described herein do not contain the molecular form of the antibody in an amount sufficient to have biological activity attributed to such molecular form. The biological activity of the combination drug (combination pharmaceutical composition) of the invention is amply demonstrated in the appended examples.

In one embodiment, the invention provides a method of treating a patient suffering from respiratory tract disorders or conditions, by administration of a combination pharmaceutical composition wherein the composition comprises a) an activated-potentiated form of an antibody to bradykinin, b) an activated-potentiated form of an antibody to histamine and c) an activated-potentiated form of an antibody to morphine.

In a preferred embodiment the respiratory tract disorder or condition is viral respiratory tract infection.

In another preferred embodiment the respiratory tract disorder or condition is acute upper respiratory tract disorder.

In a preferred embodiment the respiratory tract disorder or condition is chronic upper respiratory tract disorder.

In another embodiment, the invention provides a method of treating a patient suffering from symptoms of upper respiratory tract disorder or condition, by administration of a combination pharmaceutical composition, wherein the composition comprises a) an activated-potentiated form of an antibody to bradykinin, b) an activated-potentiated form of an antibody to histamine and c) an activated-potentiated form of an antibody to morphine.

In a preferred embodiment the symptom of respiratory tract disorder or condition is cough.

Preferably, for the purpose of treatment, the combination of the invention is administered from once daily to four times daily, preferably twice daily, each administration including one or two combination unit dosage forms.

The invention is further illustrated with reference to the appended non-limiting examples.

EXAMPLES

Example 1

Thirty male guinea pigs weighing 350-400 g were used in the experiments. Cough was induced by inhalation of capsaicin at 30 μM using nebulizer for 5 minutes. The numbers of coughing episodes were counted for 15 minutes. Cough was induced twice—once prior to the drug administration (baseline) and second after administration. The control group (120 μL/guinea pig), was administered distilled water. Second group (40 μL/guinea pig) was administered ultra-low dose antibodies to morphine. Third group (120 μL/guinea pig) was administered the combination of ultra-low dose antibodies to bradykinin (ULDB), ultra-low dose antibodies to histamine (ULDH) and ultra-low dose antibodies to morphine (ULDM). Administration was per os (oral drops) 3 times with 120-min interval, the last time 15 min prior to capsaicin-induced cough.

The study revealed that complex combination drug ULDB+ULDH+ULDM exerts more significant antitussive effect than ULDM separately. The drugs caused cough inhibition by 55.2% and 21.5%, respectively ($p<0.05$) (See Table 1).

TABLE 1

Effect of study drugs on the number of cough episodes, M ± m

| Groups of animals | Mean number of cough episodes | | Cough inhibition |
|---|---|---|---|
| N = 10 | Baseline | After treatment | (% from baseline) |
| Control (distilled water) | 9.6 ± 1.2 | 8.4 ± 0.9 | 11.2 ± 3.1% |
| ULDM | 11.7 ± 0.6 | 9.2 ± 0.5*** | 21.5 ± 1.2%# |
| ULDB + ULDH + ULDM | 11.6 ± 0.5 | 5.2 ± 0.3*** | 55.5 ± 1.8%## |

Differences are statistically significant as compared to the baseline: ***$p < 0.001$
Differences are statistically significant as compared to the control: #$p < 0.05$; ##$p < 0.01$

Example 2

Tablets weighting 300 mg saturated with pharmaceutical composition containing water-alcohol solutions (6 mg/tablet) activated-potentiated forms of polyclonal rabbit affinity purified ultra-low dose antibodies to bradykinin (ULDB), ultra-low dose antibodies to histamine (ULDH) and ultra-low dose antibodies to morphine (ULDM) were used which were obtained as a result of ultra high dissolution of basic stock solution in $100^{12}$, $100^{30}$, $100^{50}$ times, which are equivalent to mixture of homeopathic dissolutions C12, C30, C50.

Efficacy and safety of complex combination ULDB+ULDH+ULDM were assessed based on the results of open-label observational clinical study enrolling 107 subjects aged 19-82 years (mean age 47.60±11.56 years) being on outpatient treatment due to viral upper respiratory infection (URI) (acute pharyngitis/rhinopharyngitis, acute laryngitis/laryngotracheitis) and/or lower respiratory infections (acute bronchitis). The main symptom of viral URI's of this localization, beside fever, intoxication and catarrhal symptoms, is cough which at the onset of the disease was dry (non-productive) and was registered in 100% subjects. The vast majority of patients (n=101; 94%) were enrolled into the study during the first day of viral URI's onset. 43% subjects were males (n=46), 57%—females (n=61). Almost half of patients (n=46; 43%) had moderate baseline condition, 3 (2.8%)—severe and in 58 (54%) it was not changed. Mean heart rate was 78.40±0.27 bpm, respiration rate—20.40±0.14 per minute. All subjects had increased temperature varying within 37.0-38.5° C. (in 91%) and 38.6-39.0° C. (in 9%). All patient at the beginning of the study complained of asthenic symptoms (malaise, poor appetite, myalgia), some of them—of headache (5.6%), dizziness (2.8%), adynamia (5.6%). At the baseline a patient had 5.50±0.06 coughing episodes on average; each of them consisted of 4.30±0.13 coughs. In majority subjects cough was accompanied by change of skin colour (n=107; 100%), jugular venous distention (n=107; 100%), change of postural pose (n=104; 97%). Among other catarrhal symptoms laboured nasal breath (n=107; 100%), serous nasal discharge (n=19; 18%) were observed. Objective examination showed laboured inspiration (n=3; 3%) or expiration (n=23; 22%), diffuse dry rales in lungs (n=33; 31%), general cerebral symptoms (n=2; 2%). Additional methods carried out as indicated confirmed infectious inflammatory process of respiratory tract as a cause of cough in patients enrolled into the study. Particularly, ENT-examination in majority patients enable localization of upper respiratory damage, radiological study (in bronchitis) revealed changes in lung pattern in the absence of infiltrative and focal lung lesions. Blood analysis of all study subjects showed normal or insignificant increase in leukocyte count, sometimes—insignificant leucopenia (n=9; 8%), lymphocytosis—n=12; 11%), monocytosis (n=7; 6%); ESR remained unchanged in majority (n=103; 96%) of patients. All subjects received the complex therapy ULDB, ULDH and ULDM, including, apart from rotavirus, antipyretic, detoxication and local (decongestant) drugs, 91 tablet) 4 times within the day. Other antitussive, expectorants and mucolytics were not allowed. The patients were daily examined for 7 days, and laboratory parameters were registered at the baseline and at the end of the study. Assessment criteria for antitussive efficacy of complex combination ULDB+ULDH+ULDM included total cough duration including duration of dry cough, the number of cough episodes within the hour and mean number of coughs during one cough episode. Additional criteria included duration of other catarrhal symptoms, fever and intoxication as well as sleep disorders.

Obtained results showed positive changes characterizing cough beginning from day 1 of the complex combination ULDB+ULDH+ULDM administration. Cough intensity including the number of cough episodes and number of coughs in one episode had clear positive dynamics during the treatment. The number of cough episodes within one hour reduced from 5.50±0.06 on day 1 to 3.7±0.15 on day 2; 2.4±0.12 on day 3; 1.5±0.08 on day 4; 0.9±0.07 on day 5 and 0.4±0.02 on day 6 of observation. Mean number of cough impulses in one episode in respective days was 4.30±0.13; 4.10±0.30; 3.20±0.15; 2.60±0.12; 1.40±0.06 and 0.30±0.01. Dry cough was eliminated within 4.20±0.19 days, by the end of which it transformed into productive cough lasting no more than until day 7 (mean duration of cough was 6.60±0.05 days).

Comparison of treatment results with the ones obtained in studies performed and published earlier (see Table 2) showed more evident antitussive efficacy of the complex combination ULDB+ULDH+ULDM as compared to stoptussin® and erespal® when treating viral URI's in adults. Stoptussin® treatment ensured transformation of dry cough into productive one within 6.2 days (vs. 4.20±0.19 days when using the complex combination ULDB+ULDH+ULDM) on average. Total duration of cough was 8.8 days when using stoptussin® and more than 7 days—erespal® (vs. 6.60±0.05 days—when using the complex combination ULDB+ULDH+ULDM).

Other symptoms accompanying cough, regressed on days 3-4 of therapy with the complex combination ULDB+ULDH+ULDM. Change of skin colour during cough persisted until day 2.8±0.1, swelling of jugular veins—until 3.7±0.09 day, change of posture—until 2.7±0.11 day.

Anti-inflammatory activity of components included into the complex combination ULDB+ULDH+ULDM was demonstrated as positive changes in intoxication and catarrhal symptoms of viral URI's (Table 3). Constant fever depending on severity of the disease was observed for 2.90±0.08 days with periodic body temperature increase in certain cases up to day 4 of the disease (4.00±0.08). Relief of nasal breathing was noted as soon as by the end of day 4 (4.3±0.12) of the treatment, rhinitis—day (2.2±0.1). Complete elimination of catarrhal symptoms in mouth mucosa took place within 6.9±0.08 days. The time to eliminate intoxication signs was about 4 days: asthenia persisted for 3.60±0.09 days on average; poor appetite—3.00±0.07 days; general cerebral symptoms—3.00±0.01 days. Sleep tended to normalize within 3.80±0.09 days.

The results obtained were comparable to data on efficacy of viral URI treatment using other antitussive drugs. Stoptussin® reduced severity of intoxication and catarrhal symptoms by day 5 of the treatment (Sirotina E. V., 2009); erespal® significantly reduced clinical signs of viral URI's for 7 days, however, some symptoms, e.g. nasal congestion persisted after the end of the treatment in more than 20% of the subjects (Plusa T., Navatska D., 2000).

Safety analysis included data of all 107 subjects who were enrolled into the study and completed the treatment within the terms established by the protocol. No subjects withdrew from the study before completion. During the entire observation period good drug tolerability was observed. No adverse events associated with the use of the complex combination ULDB+ULDH+ULDM were registered. No cases of refusal to take the complex combination drug were reported. Blood analysis at the end of the treatment did not reveal any pathological deviations (Table 4). Urinalysis on the first and last days of the study did not reveal any pathology in patients.

Thus, the study results confirmed efficacy of the complex combination ULDB+ULDH+ULDM in the treatment of cough in adults with viral URI's. Antitussive efficacy was demonstrated as reduced cough intensity (number of episodes within the hour and number of cough jerks in one episodes), beginning from the first days of the treatment. Mean duration of dry (non-productive) and wet (productive) cough was shorter as compared to other antitussive drugs. The complex combination ULDB+ULDH+ULDM, inhibited cough reflex and reduced severity of infectious inflammation of respiratory tract (the cause of cough in viral URI), which in turn resulted in faster positive changes of intoxication and catarrhal symptoms. Clinical signs of the disease regressed mainly within the first 3-4 days. Absence of adverse events and pathological deviations of laboratory parameters associated with the use of the complex combination ULDB+ULDH+ULDM evidences the drug safety.

TABLE 2

Comparative efficacy data of antitussive drugs

| Drugs | Time to cough relief (days) | Time to develop first episodes of productive cough (days) |
|---|---|---|
| Combination of ULDB + ULDH + ULDM | 6.60 ± 0.05 | 4.20 ± 0.19 |
| Stoptussin ® (Sirotina E. V., 2009) | 8.8 | 6.2 |
| Erespal ® (Plusa T., Navatska D., 2000) | >7 | — |

TABLE 3

Duration of viral URI clinical symptoms

| | Clinical signs | Days |
|---|---|---|
| | Fever | 4.00 ± 0.08 |
| Catarrhal symptoms | Hoarse voice | 3.10 ± 0.12 |
| | Laboured nasal breathing | 4.30 ± 0.12 |
| | Serous nasal discharge | 2.20 ± 0.10 |
| | Catarrhal signs in mouth mucosa | 6.90 ± 0.08 |
| Intoxication symptoms | General malaise | 3.60 ± 0.09 |
| | Sleep disorder | 3.80 ± 0.09 |
| | Poor appetite | 3.00 ± 0.07 |
| | General cerebral symptoms | 3.00 ± 0.01 |

TABLE 4

Parameters of complete blood analysis during observation

| Parameters | Visit 1 | Visit 7 |
|---|---|---|
| Erythrocytes, $\times 10^{12}$/L | 3.30 ± 0.05 | 3.10 ± 0.05 |
| Hemoglobin, g/L | 120.10 ± 1.59 | 116.80 ± 1.54 |
| Hematokrit, % | 39.90 ± 0.33 | 37.80 ± 0.42 |
| Platelets, $\times 10^9$/L | 268.50 ± 3.67 | 262.60 ± 3.37 |
| ESR, mm/hour | 15.90 ± 0.56 | 7.301 ± 0.37 |
| Leukocytes, $\times 10^9$/n | 14.10 ± 0.52 | 6.701 ± 0.48 |
| Stab leeukocytes, % | 9.9 ± 0.3 | 6.80 ± 0.21 |
| Segmented leeukocytes, % | 52.8 ± 0.7 | 58.40 ± 0.54 |
| Basophiles, % | 0.1 ± 0.03 | 0.10 ± 0.02 |
| Eosinophiles, % | 3.10 ± 0.29 | 2.80 ± 0.25 |
| Lymphocytes, % | 30.50 ± 0.68 | 28.09 ± 0.57 |
| Monocytes, % | 2.90 ± 0.21 | 3.10 ± 0.21 |

Example 3

Tablets weighting 300 mg were used. The tablets were impregnated with solutions (6 mg/tablet) of ultra-low doses of rabbit polyclonal affinity-purified antibodies against bradykinin (ULDB), histamine (ULDH) and morphine (ULDM), each obtained as a result of hyper-dilution of matrix solutions in $100^{12}$, $100^{30}$, $100^{50}$ times, which are equivalent to mixture of homeopathic dissolutions C12, C30, C50.

The evaluation of efficacy and safety of the complex composition ULDB+ULDH+ULDM was based on multicenter open—label comparative clinical study being still lo conducted. At present, data on 20 patients having completed the therapy is available. Fourteen patients received the complex composition ULDB+ULDH+ULDM at a dose of 2 tablets 3 times a day for the first 3 days, 1 tablet 3 times a day for 4 subsequent days. Six patients received Kodelak® (codeine+ sodium hydrocarbonate+licorice roots+herb of Thermopsis lanceolata), tablets (JSC Pharmstantard—Leksredstva, Russia), at a dose of 1 tablet 3 times a day. In the both groups therapy duration was 7 days.

Outpatient men and women over 18, having diagnosed viral URI's with non-productive cough on the background of developing acute pharyngitis, laryngitis, laryngotracheitis, tracheitis, tracheobronchitis, and bronchitis accompanied with 12 hours-7 days cough duration were enrolled in the study. Prior to all procedures the subjects signed Informed consent form in order to participate in the study. The patients were examined; blood and urine samples were collected to control the therapy safety.

The analysis of the drug therapeutic efficacy was based upon the availability of cough and its type being manifested at the visits (at the baseline (therapy onset), on days 2, 4 and 7 of the treatment) as well on the basis of the data contained in patients' diaries.

The proportion of patients with registered at the visits cough relief and transformation of non-productive to productive cough as well as intensity of daytime and night coughing evaluated based on Cough intensity scale contained in patient diary were compared at each visit. In both groups patients with cough relief were registered at the last visit only (day 7±1 of the treatment). In Kodelak® group such patients comprised 83.3% while in the complex composition ULDB+ULDH+ULDM group it was 73.8%; no significant difference between the groups was achieved.

The proportion of patients with transformation from non-productive cough to productive one in the complex composition ULDB+ULDH+ULDM group was 28.6% and in the Kodelak® group—20.0%. On day 4 and day 7 these proportions were 35.7 and 16.7% the complex composition ULDB+ULDH+ULDM group and in the Kodelak® group, respectively. No significant difference between the groups was achieved.

Figure 1:
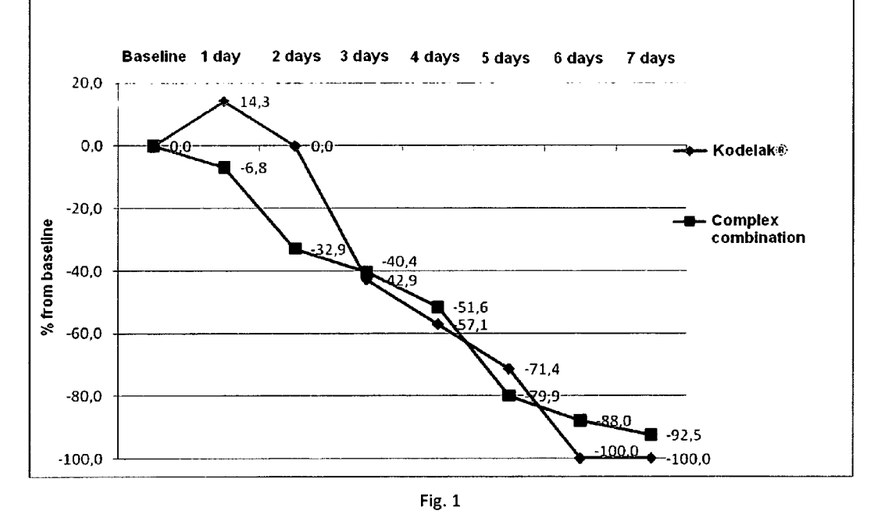
FIG. 1—Shows the changes in night coughing intensity evaluated based on Cough intensity scale, changes in mean score I groups (%)
Figure 2:
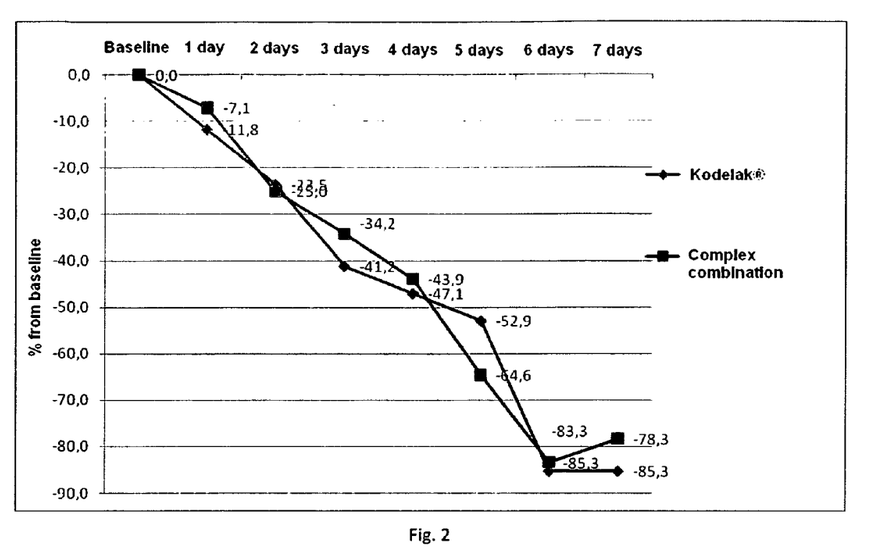
FIG. 2—Shows the changes in daytime coughing intensity evaluated based on Cough intensity scale, changes in mean score I groups (%).

Data on changes in cough intensity are presented on FIGS. 1 and 2. It should be noticed that 2-fold reduction in daytime and night coughing was reached in both groups by day 4 of treatment for night coughing and by day 5 of the therapy for daytime coughing.

The results obtained show that the anti-cough effect of the complex composition ULDB+ULDH+ULDM is comparable to that of the anti-cough effect of Kodelak®.

Lack of adverse events related to administration of the complex composition ULDB+ULDH+ULDM and absence of pathological deviations in laboratory parameters confirm the drug safety.

Example 4

Tablets weighting 300 mg were used. The tablets were impregnated with solutions (6 mg/tablet) of ultra-low doses of rabbit polyclonal affinity-purified antibodies against bradykinin (ULDB), histamine (ULDH) and morphine (ULDM), each obtained by hyper-dilution of matrix solutions in $100^{12}$, $100^{30}$, $100^{50}$ times, which are equivalent to mixture of homeopathic dissolutions C12, C30, C50.

To evaluate the efficacy and safety of the complex combination ULDB+ULDH+ULDM in the treatment of cough in children open observation clinical study was conducted, in which 100 inpatients and outpatients aged 1-3 years with diagnosed acute laryngitis/laryngotracheitis on the background of viral URI's were enrolled. The mean age of the patients was 1.4±0.1 years; boys comprised 57% of the subjects. All the patients were enrolled in the study within the first (57%) or in rare cases within the second (43%) day after the onset of viral URI's development. Armpit temperature in 90% of the subjects did not exceed 38.5° C. Frequent dry (non-productive) cough was the main sign at the onset of the disease; in the majority of children dry rough hacking cough sometimes causing vomiting and disturbing the children's sleep was registered. Mean basic cough frequency was 2.90±0.27 episodes per hour; the mean number of cough jerks within 1 episode was 4.80±0.28. In the vast majority of children (97%) labored nasal breathing with poor serous drainage from nasal ways (90%). In 60% of children sleep disorders caused by frequent cough were observed. Besides antiviral, antipyretics, disintoxicants and local (decongestants) combined therapy included the complex combination ULDB+ULDH+ULDM (1 tablet preliminary dissolved in 1 tea spoon of boiled water cooled to room temperature 4 times a day). During the study no other anti-cough, expectorants and mucolytics were administered. For 7 days physician daily examined the subjects; at the baseline and at the end of the study laboratory parameters were registered. Total cough duration including duration of dry cough and terms to its transfer to wet cough (productive), the number of cough episodes/hour and the mean number of cough jerks per 1 episode were used as efficacy criteria. Besides changes in other viral URI's signs—catarrhal symptoms manifested by respiratory tract, general toxic symptoms as well as sleep disorders caused by cough were registered.

The analysis of the obtained results showed that administration of the complex combination ULDB+ULDH+ULDM caused positive changes in the parameters characterizing the duration, nature and intensity of cough. The total duration of the cough was 4.40±0. 28 days including the duration of dry cough 4.1±0.27 days; first episodes of productive cough were observed on day 2.40±0.05. The parameters of cough intensity—the number of cough episodes per hour and the number of coughs per 1 episode—have changed distinctly under the treatment. The number of cough episodes changed as follows: on day 1 of the therapy—2.90±0.27; on day 2 of the therapy 2.30±0.12; on day 3—1.70±0.12; on day 4—0.80±0.01; on day 5—0.40±0.01; on day 6—0.20±0.01; on day 7—0.10±0.01. The number of coughs per 1 episode—on day 1 of the therapy was 5.00±0.22; on day 2—4.50±0.20; on day 3—3.60±0.30; on day 4—2.60±0.13; on day 5—1.80±0.12; on day 6—0.90±0.07; on day 7—0.20±0.01.

The comparison of the obtained results of the treatment with literature data (Table 5) showed that the effect of the complex combination ULDB+ULDH+ULDM on total cough duration and time to formation of productive cough was comparable to that of anti-cough drugs used for pediatric application including combined anti-cough drug Kodelak fito® (Pharmstandard, Russia) and Prospan® (KARL ENGELHARD GmbH & Co., Germany-Russia).

Therapeutic efficacy of the complex combination ULDB+ULDH+ULDM was also confirmed by sleep disorders eliminations in children. On the whole sleep disorders retained for 1.80±0.18 days (1-2 days variation). To compare things it should be noted that the administration of complex drug Doctor Mom® in the treatment of cough in children caused sleep normalization by day 4 in 63% of patients.

The evaluation of other clinical signs showed rapid reverse development of the main viral URI's symptoms. Body temperature normalization was observe on day 2.7±0.19; general malaise retained 1.70±0.08 days; poor appetite—2.10±0.16 days; irritability/capriciousness—2.00±0.13 days. Catarrhal symptoms of upper respiratory tract completely eliminated in all the subjects within the first 7 days after the onset of viral URI's development; at that hoarse voice and labored nasal breathing (both symptoms retained for 1.0±0.00 days at average) were the first to eliminate, nasopharynx inflammation retained longer (6.40±0.19 days). But the comparison of the treatment results with literature data showed considerable effect of the complex combination ULDB+ULDH+ULDM on the main viral URI's clinical symptoms. Particularly according to the study conducted by O. Zaitseva (2008)

recovery in children with viral URI's provided that kodelak fito was included in the combined therapy was observed on day 7.7±0.3, other mucolytics—on day 8.9±0.3. The use of the complex combination ULDB+ULDH+ULDM in the therapeutic complex caused the reduction in viral URI's course up to 6.40±0.19 days.

Safety analysis was based on data of all patients involved in the study (n=100). No adverse events related to the drug administration were registered. The study of laboratory parameters including complete blood cells account, biochemical blood cells account and urine analysis did not reveal any significant deviations from normal values.

Thus the study showed the efficacy of the complex combination ULDB+ULDH+ULDM in the treatment of cough in children with viral URI's, which was manifested in the reduction in the duration and intensity of dry (non-productive) and wet (productive) cough as compared to the similar values of other anti-cough drugs in children.

The efficacy of the complex combination ULDB+ULDH+ULDM caused by its ability to inhibit cough reflex and to reduce the intensity of respiratory tract infections leading to cough development was confirmed by rapid positive changes in the main clinical symptoms—general malaise and catarrh, which were completely eliminated in all the patients within 7 days from viral URI's onset. Monitoring of potential adverse events in the course of the treatment and repeated study of laboratory parameters proved the drug safety.

TABLE 5

Comparative data on the efficacy of anti-cough drugs

| Drugs | Time to cough relief (days) | Time to appearance of first episodes of productive cough (days) |
| --- | --- | --- |
| Composition ULDB + ULDH + ULDM | 4.4 ± 0.28 | 2.40 ± 0.05 |
| Kodelak fito ® (Elkina T. N., 2006) | Day 5 | Day 3 |
| Prospan ® (Zaitseva O. V. et al 2006; Ovsyannikova E. M. et al, 2007) | Day 5 | Day 5 |

What is claimed is:

1. A combination pharmaceutical composition comprising a) homeopathically activated-potentiated form of an antibody to bradykinin, b) an activated-potentiated form of an antibody to histamine and c) an activated-potentiated form of an antibody to morphine.

2. The combination pharmaceutical composition of claim 1, wherein the homeopathically activated-potentiated form of the antibody to bradykinin having SEQ ID NO:1.

3. The combination pharmaceutical composition of claim 1, wherein the homeopathically activated-potentiated form of the antibody to bradykinin is in the form of a mixture of C12, C30, and C50 homeopathic dilutions impregnated onto a solid carrier and the homeopathically activated-potentiated form of the antibodies to histamine and the homeopathically activated-potentiated form of the antibody to morphine are in the form of mixture of C12, C30, and C50 homeopathic dilutions impregnated onto said solid carrier.

4. The combination pharmaceutical composition of claim 3, wherein said carrier is impregnated with a mixture of said dilutions.

5. The combination pharmaceutical composition of claim 1, wherein the homeopathically activated-potentiated form of the antibody to bradykinin is a monoclonal, polyclonal or natural antibody.

6. The combination pharmaceutical composition of claim 5, wherein the homeopathically activated-potentiated form of the antibody to bradykinin is a polyclonal antibody.

7. The combination pharmaceutical composition of claim 1, wherein the homeopathically activated-potentiated form of the antibody to histamine is a monoclonal, polyclonal or natural antibody.

8. The combination pharmaceutical composition of claim 7, wherein the homeopathically activated-potentiated form of the antibody to histamine is a polyclonal antibody.

9. The combination pharmaceutical composition of claim 1, wherein the homeopathically activated-potentiated form of the antibody to morphine is a monoclonal, polyclonal or natural antibody.

10. The combination pharmaceutical composition of claim 9, wherein the homeopathically activated-potentiated form of the antibody to morphine is a polyclonal antibody.

11. The combination pharmaceutical composition of claim 1, wherein said homeopathically activated-potentiated forms of antibodies prepared by successive multiple dilutions in a solvent selected from the group comprising water and a mixture of water and ethanol, coupled with shaking of every dilution.

* * * * *

---

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 1

Arg Pro Pro Gly Phe Ser Pro Phe Arg
1               5
```